United States Patent
Luchetti

(10) Patent No.: US 7,594,914 B2
(45) Date of Patent: Sep. 29, 2009

(54) INCISION AND CLOSURE SURGICAL DEVICE

(76) Inventor: Pablo Cristian Luchetti, M. Piaggio 549, Lomas de Zamora, Buenos Aires (AR) 1832

( * ) Notice: Subject to any disclaimer, the term of this patent is extended or adjusted under 35 U.S.C. 154(b) by 565 days.

(21) Appl. No.: 11/539,176

(22) Filed: Oct. 6, 2006

(65) Prior Publication Data
US 2007/0088339 A1   Apr. 19, 2007

(30) Foreign Application Priority Data
Oct. 7, 2005   (AR) ............................... P050104223

(51) Int. Cl.
A61B 18/18 (2006.01)
(52) U.S. Cl. ............... 606/41; 606/49; 606/215; 606/216; 606/217; 606/50
(58) Field of Classification Search .................. 606/41, 606/49, 50, 167, 215–217; 383/63, 64
See application file for complete search history.

(56) References Cited

U.S. PATENT DOCUMENTS

| 2,012,755 | A | | 8/1935 | De Muth | |
|---|---|---|---|---|---|
| 2,752,921 | A | | 7/1956 | Fink | |
| 2,873,741 | A | | 2/1959 | Donaldson | |
| 3,516,409 | A | * | 6/1970 | Howell | 606/217 |
| 3,568,276 | A | * | 3/1971 | Morgan | 27/21.1 |
| 3,983,878 | A | | 10/1976 | Kawchitch | |
| 4,114,624 | A | * | 9/1978 | Haverstock | 606/167 |
| 4,467,805 | A | | 8/1984 | Fukuda | |
| 4,535,772 | A | | 8/1985 | Sheehan | |
| 4,657,016 | A | | 4/1987 | Garito | |
| 4,881,546 | A | | 11/1989 | Kaessmann | |
| 4,905,694 | A | * | 3/1990 | Will | 606/217 |
| 5,377,695 | A | * | 1/1995 | An Haack | 128/888 |
| 5,584,856 | A | | 12/1996 | Jameel | |
| 5,669,934 | A | | 9/1997 | Sawyer | |

(Continued)

OTHER PUBLICATIONS

Onuminya Je, Alufohai E, Onuminya DS. Outcome of surgical zipper technique. Journal of the National Medical Association. J Natl Med Assoc. Jan. 2006;98(1):83-5. United States.

(Continued)

*Primary Examiner*—Linda C Dvorak
*Assistant Examiner*—Amanda Scott

(57) ABSTRACT

Incision and closure surgical device designed to assist in operative surgery as a means of effecting and repairing skin wounds. A slide fastener is fitted to a self-adhesive sheet that is attached to the skin surface. The slider of the slide fastener contains a contact electrode for electrocoagulation fitted with a cutting edge. As the slide fastener is opened, the slider simultaneously effects the incision by means of the cutting edge of the electrode, severing both the flexible sheet and the skin beneath. For closing the incision, the stringer tapes of the slide fastener interlock by the action of the slider, thereby bringing both the edges of the flexible sheet and the wound beneath into apposition. As the slider is drawn forwards closing the stringer tapes, electrical energy is applied by the electrode at the union site of the wound edges, which have previously been brought into apposition by the mechanical action of the slide fastener, thus ensuring that the edges become adhered in full depth as a result of electrical coagulation.

6 Claims, 6 Drawing Sheets

U.S. PATENT DOCUMENTS

| | | |
|---|---|---|
| 5,759,193 A | 6/1998 | Burbank |
| 5,769,848 A | 6/1998 | Wattanasirichaigoon |
| 5,814,067 A | 9/1998 | Fleischmann |
| 6,010,516 A | 1/2000 | Hulka |
| 6,224,593 B1 | 5/2001 | Ryan |
| 6,638,273 B1 | 10/2003 | Farley |
| 6,645,205 B2 | 11/2003 | Ginn |
| 6,860,895 B1 | 3/2005 | Akerfeldt |

OTHER PUBLICATIONS

Brega-Massone PP, Lequaglie C, Magnani B, Cataldo I. A new proposal of skin-closure system for median sternotomy: usefulness and cosmetic results analysis of MEDIZIP Surgical Zipper in neoplastic immuno-compromised patients. Journal of surgical oncology.

Bastian PJ, Haferkamp A, Albers P, Muller SC. [Medizip surgical zipper: a new form of non-invasive wound closure with a surgical zipper] Aktuelle Urologie. Aktuelle Urol. Oct. 2003:34(6):398-401. German.

Zutt M, Emmert S, Hanssle H, Grafe A, Domhof S, Neumann C, Kretschmer L. [Improved scar formation after using a medical surgical zipper for wound closure under tension] Der Hautarzt; Zeitschrift für Dermatologie, Venerologie, und verwandte Gebiete. Hautarzt. Apr. 2003:54(4):342-7. Epub Mar. 4, 2003 German.

Carcoforo P, Jorizzo EF, Maestroni U, Soliani G, Navarra G. A new device for sutureless skin closure "the zipper". Annali italiani di chirurgia. Ann Ital Chir. Jan.-Feb. 2002;73(1):75-9; discussion 79-80. Italy.

Risnes I, Abdelnoor M, Lundblad R, Baksaas ST, Svennevig JL. Sternal wound closure in patients undergoing open-heart surgery: a prospective randomized study comparing intracutaneous and zipper techniques. European journal of cardio-thoracic surgery : official journal of the European Association for Cardio-thoracic Surgery. Eur J Cardiothorac Surg. Aug. 2002:22(2):271-7.

Shields CA, Schechter DA, Tetzlaff P, Baily AL, Dycus S, Cosgriff N. Method for creating ideal tissue fusion in soft-tissue structures using radio frequency (RF) energy. Surgical technology international. Surg Technol Int. 2004:13:49-55.

Heniford BT, Matthews BD, Sing RF, Backus C, Pratt B, Greene FL. Initial results with an electrothermal bipolar vessel sealer. Surgical endoscopy. Surg Endosc. Aug. 2001;15(8):799-801. Epub May 14, 2001. Germany.

Bass LS, Popp HW, Oz MC, Treat MR. Anastomosis of biliary tissue with high-frequency electrical diathermy. Surgical endoscopy. Surg Endosc. 1990;4(2):94-6. Germany.

Imakiire N, Kotani A, Ishii Y. Experimental study on thermal welding for the knee meniscal white zone. Journal of orthopaedic science : official journal of the Japanese Orthopaedic Association. J Orthop Sci. 2003;8(5):683-92. Japan.

* cited by examiner

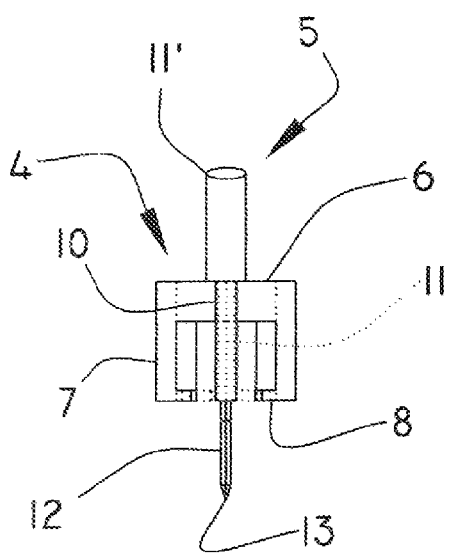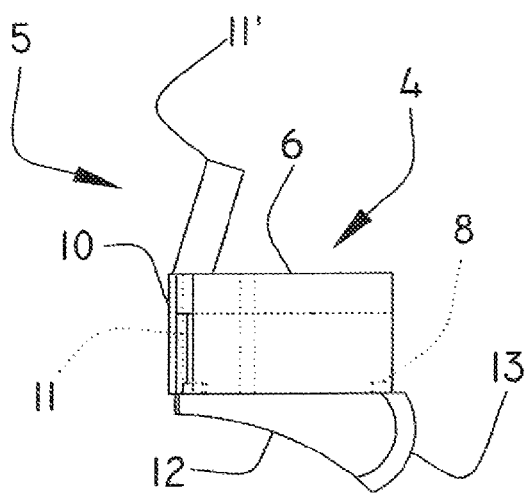
FIG. 7
FIG. 8
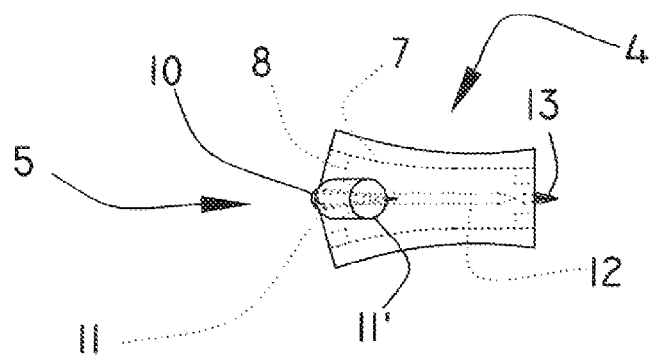
FIG. 9

INCISION AND CLOSURE SURGICAL DEVICE

FIELD OF THE INVENTION

The present device embraces the technical field of medical science, and the branch of surgery in particular. Within surgery, the present device falls into two large classes of surgical instruments or devices. On the one hand, it is classified as a mechanical surgical device because it involves a cutting surgical appliance and an instrument for closing wounds. On the other hand, as it makes use of a contact electrode for electrical coagulation, which operates by applying electrical energy to the body, it is also classified among the instruments that transmit non-mechanical energy to the body.

BACKGROUND OF THE INVENTION

In connection with the previous art specifically designed for effecting and repairing skin surgical wounds, the present invention is closely related to:

A) Devices or instruments that include a groove or track to direct the motion of a surgical device as a skin incision is effected. Some examples of these are the U.S. Pat. Nos. 3,526,409; 4,114,624; 3,983,878; 4,467,805 and 3,568,276.

Although the aforesaid devices permit the control of the length and shape of an incision, none of them limits the depth of the skin cut. Unlike the previous technical inventions, the cutting surgical element in our present device is fitted and secured to a member that compresses the skin surface, thus preventing an unwanted deeper cut from occurring.

B) Devices or instruments that include a means for bringing the edges of the wound together without sutures or staples. Some examples of these are the U.S. Pat. Nos. 5,759,193; 5,814,067; 5,584,856 and 6,860,895 B1. Within this group, the devices that most closely resemble the present invention include an adhesive flexible sheet placed upon opposite sides of the wound, which becomes the structural means upon which a slide fastener or zipper operates to close the incision. In some cases, such strip is initially a single member which is later severed together with the skin as the incision is effected. In other cases, the strip consists of two separate members prior to effecting the incision. Some examples of these are the U.S. Pat. Nos. 4,905,694; 2,012,755; 2,873,741; 2,752,921; 4,881,546; 5,377,695 and 4,535,772.

Even if the aforesaid devices avoid the use of sutures or staples to close an incision, some of them employ clamps or jagged elements that may additionally damage the skin tissue. Those devices which do not pierce through the skin to fasten the edges of the wound can only close the skin superficially, thus preventing the edges from being brought together with equal force along the full depth of the wound. In such cases an unwanted opening may occur beneath the superficial skin union, which is likely to breed purulent, serum or haematic collections, as well as increase the chances of a non-aesthetic healing. In none of the aforementioned cases does the risk of hemorrhage decrease as compared to that of an ordinary suture.

Unlike the previous art, the present invention fastens the edges of the wound producing no additional damage and attains a strong and early union of the edges of the incision in full depth. By the action of the slide fastener or zipper the superficial edges of the wound are brought together while the electrical coagulation fastens those edges in full depth. Besides bracing the union, the rapid wound coagulating process reduces the risk of hemorrhage and creates a physical barrier that blocks the access to infectious agents.

C) Devices or instruments that include contact electrodes designed for a special kind of electrical coagulation (i.e. electrocoaptation) employed to effect the union or coaptation of portions of body tissues. The present invention is also related to other instruments that utilize contact electrodes supplied with a cutting surgical device. Some examples of these are found among U.S. Pat. Nos. 4,657,016; 6,010,516; 6,638,273 B1; 5,669,934; 6,224,593 B1; 5,769,848 and 6,645,205 B2.

In all abovementioned cases, the electrical coaptation technique is applied by means of electrodes made up of two pincer-like terminal members used to bring both parts of body tissue together and later join them by means of electrical coagulation. No device within this group is designed for the closure of a skin wound or could be employed successfully to that end. Moreover, among the existent technical devices, the electrodes supplied with a cutting edge are designed for severing portions of tissue by means of electrical energy as well as for applying electrical coagulation on the edges of a wound as the incision is being effected, thus avoiding the hemorrhage of the severed tissue while the wound remains open. None of these electrodes with cutting edges is currently employed to close or coagulate a wound while it is being repaired.

By contrast with the previous art, the present invention includes a one-member contact electrode supplied with a cutting edge that is employed to effect an incision as well as to close the edges of a skin wound by means of electrical coaptation. The incision on the skin is effected by the cutting edge without recourse to electrical energy. During the closure of an incision, as the slide fastener or zipper mechanically fastens the edges of the wound, the electrode electrically coagulates the section where the edges are joined, thus fastening them in full depth.

SUMMARY OF THE INVENTION

The most salient feature of the present surgical device is a slide fastener (or zipper) fitted to a self-adhesive flexible sheet that is attached to the skin surface. The innovative feature lies in the slider of the aforesaid slide fastener or zipper. The separator island of the slider consists of a contact electrode that is made up of a vertical segment spanning the full height of the slider and a horizontal segment stretching rearward from the lower edge of the vertical segment. The rear end of the horizontal segment is fitted with a cutting edge capable of applying electrical energy to the body tissues. The said cutting edge is positioned both underneath and behind the rear end of the main body of the slider, which position allows such cutting edge to constantly remain underneath a closed segment of the slide fastener, whichever be the position of the slider along the stringer tapes.

BRIEF DESCRIPTION OF THE DRAWINGS

FIG. 7 shows an elevated front view of the slider.
FIG. 8 shows a right-hand side view of the slider.
FIG. 9 shows a top view of the slider.

DETAILED DESCRIPTION OF THE INVENTION

Figure 1:
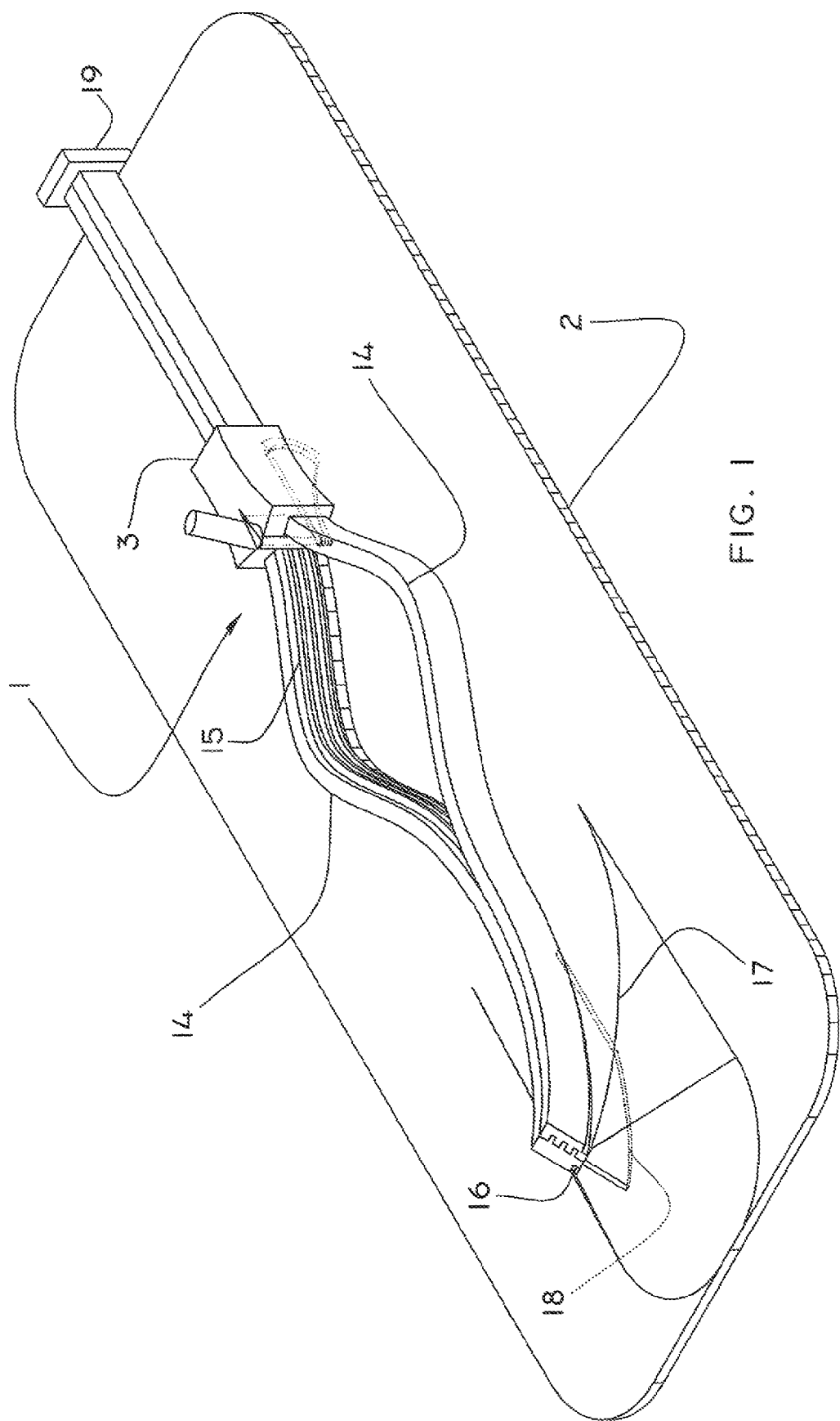
FIG. 1 is a perspective view of the surgical device.
Figure 2:
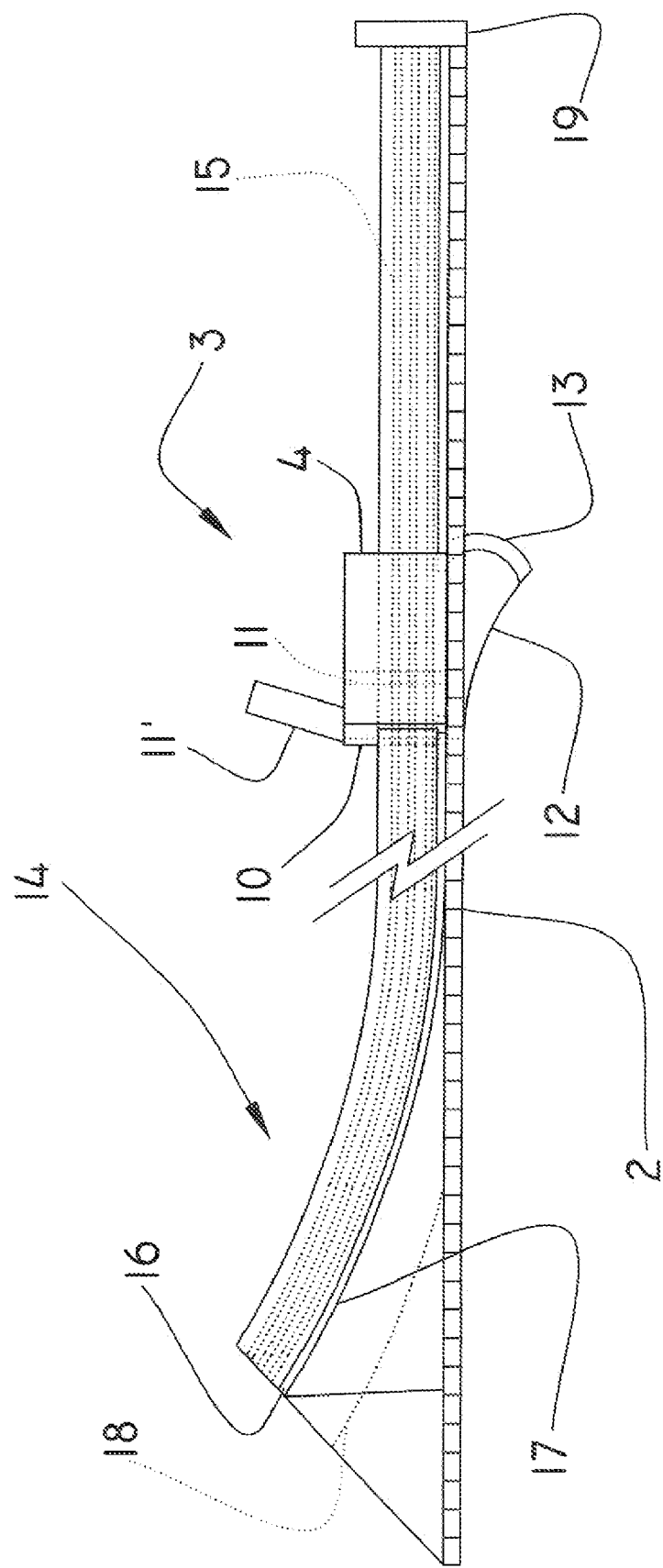
FIG. 2 is a right-hand side view of the surgical device.
Figure 3:
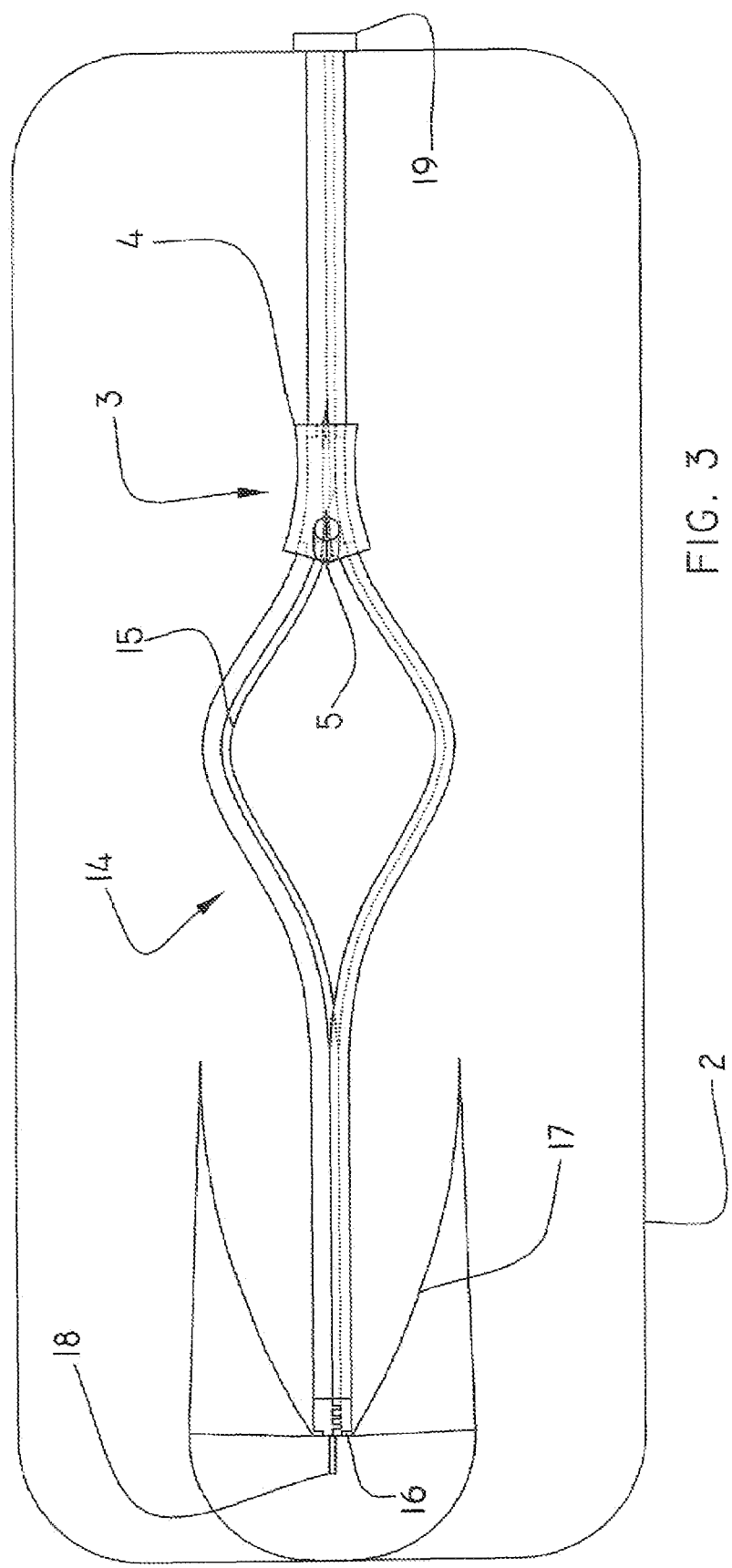
FIG. 3 is a top view of the surgical device.
Figure 4:
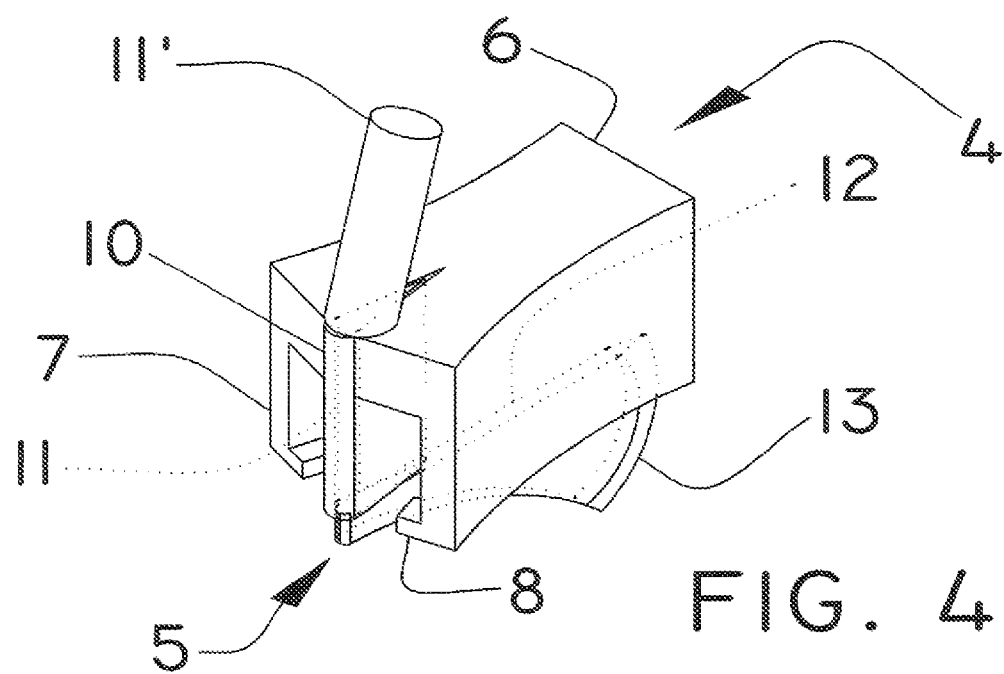
FIGS. 4 and 5 are two different perspective views of the slider.
Figure 5:
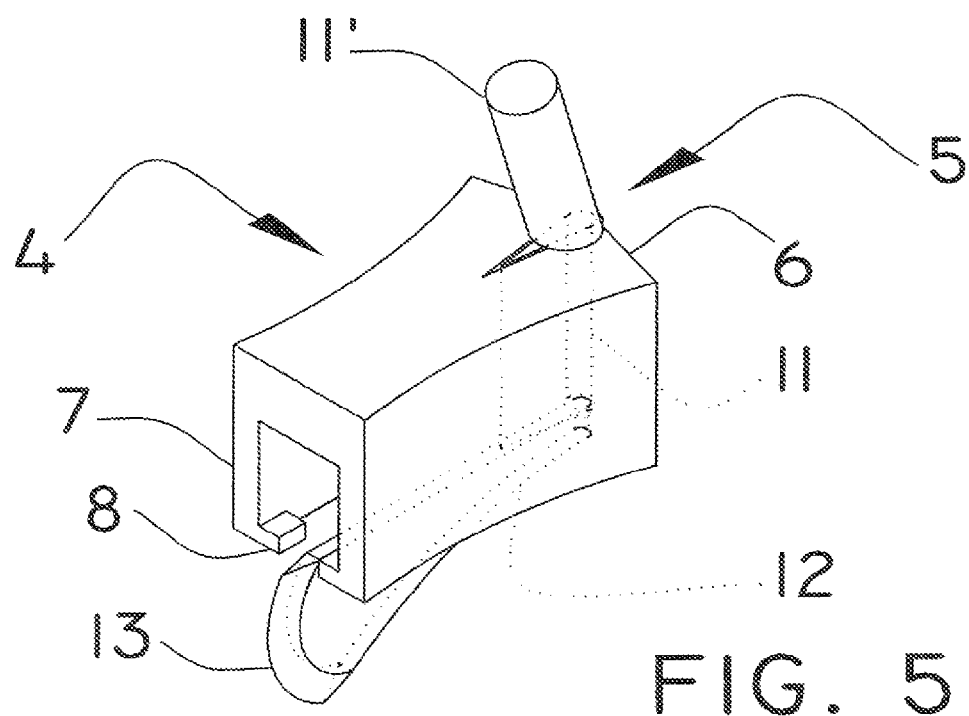
Figure 6:
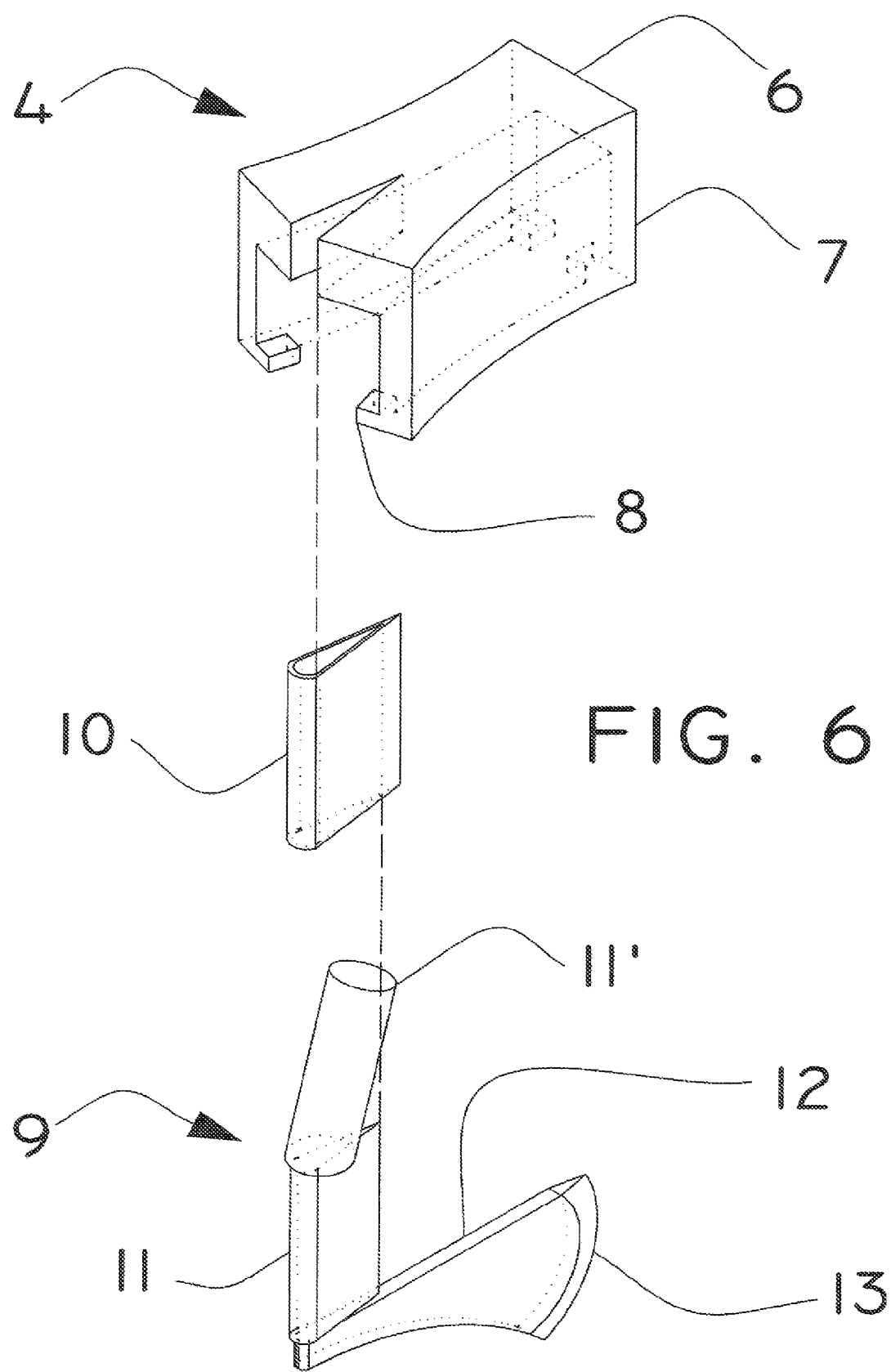
FIG. 6 is an exploded view of the slider.

In all the abovementioned figures, the same reference numbers indicate identical or corresponding elements.

The present invention consists of a slide fastener (1) attached to the surface of a self-adhesive flexible sheet (2).

The slider (3) of the slide fastener (1) is made up of a main body (4) and a separator island (5). The main body (4) consists of an upper surface (6) and two lateral walls (7), both of which are fitted with a wedge (8) in the lower edge of their respective internal faces. The said wedges interlock the lateral crevices (16) in the stringer tapes (14) of the slide fastener (1). The separator island (5) consists of an electrode (9) enclosed in a outer cover sheath (10). The electrode (9), in turn, contains a vertical segment (11) and a horizontal segment (12), which rear end is fitted with a cutting edge (13) that doubles as an active terminal for applying electrical energy to the body tissues. The upper end (11') of the vertical segment (11) serves as the terminal element for connection to an electrical surgery instrument. With the exception of the terminal (11') and the cutting edge (13), the rest of the electrode (9) is sheathed in an insulating material against electrical energy.

The stringer tapes (14) of the slide fastener (1) contain continuous cross section interlocking members (15) and lateral crevices (16) where the wedges (8) in the main body of the slider (4) interlock.

In the front part of the present device, the self-adhesive flexible sheet (2) thickens progressively, creating a slope (17) that permits the access and removal of the slider (3). The section of the slope (17) contains a carved-in furrow (18) that permits the motion of the horizontal segment (12) and the cutting edge (13) of the electrode (9).

Prior to the use of the surgical device, the stringer tapes (14) are closed and the slider (3) rests on the slope (17). The self-adhesive sheet (2) is fixed to the skin section where the surgical operation is to be performed. In order to effect an incision, the slider (3) is moved backwards in a linear motion along the slope (17).

As the incision is effected, the electrode (9) simultaneously severs the self-adhesive sheet (2) and the skin portion beneath as the stringer tapes (14) of the slide fastener (1) become disengaged. It should be noted that the cutting edge (13) effects the skin incision before the segment of the slide fastener (1) that is located immediately above it becomes disengaged. This is due to the fact that the cutting edge (13) is positioned both underneath and behind the rear end of the main body of the slider (4), thus permitting the incision to be effected accurately along the midway line of the surgical device. This position of the cutting edge (13) behind the rear end of the main body of the slider (4) ensures that the said edge (13) always remains underneath a closed segment of the slide fastener (1), whether the device is being opened or closed. The incision is terminated once the slider (3) reaches a widened section (19) at the rear end of the stringer tapes (14).

Once the surgical device and the skin portion beneath have been opened, the operator will finalize the surgical procedures by employing other instruments, and will also be capable of effecting deep skin sutures when necessary.

Once the main surgical procedure has been conducted and the subcutaneous body tissues have been repaired, the device will be utilized for the closure of the original incision.

For closing the wound, the electrode (9) is connected to a regular electrosurgical pencil through the connection terminal end (11) on the vertical segment (11). As the slider (3) is drawn forwards closing the stringer tapes (14), electrical energy is simultaneously applied thereon at the appropriate intensity and frequency in order to coagulate the severed tissues. Given the structural unity between the stringer tapes (14) and the self-adhesive sheet (2), as well as the firm adhesion of the latter to the skin surface, the stringer tapes (14), the self-adhesive sheet (2) and the skin tissue function as an undivided whole. Therefore, as the stringer tapes (14) are brought together by means of the slider (3), the edges of the self-adhesive sheet (2) and the skin beneath are likewise drawn into apposition. Since the cutting and active edge (13) always remains underneath a closed segment of the slide fastener (1), as the slider (3) fastens together the stringer tapes, the electrode (9) applies electrical energy by means of its active edge (13) to the edges of the wound that had previously been brought into apposition by the mechanical action of the slide fastener (1), thus ensuring that the edges of the wound are joined in full depth as a result of electrical coagulation.

The closing procedure ends once the slider (3) has been mechanically moved up along the slope (17) and becomes detached from the rest of the surgical device through the front edge of the stringer tapes (14). As it slides upwards along the slope, the main body (4), the vertical segment (11) and its outer cover sheath (10) move up along the surface of the slope, while the horizontal segment (12) and its cutting edge (13) slide inside the carved-in furrow (18) until they are finally removed at the front end of the device.

Once the wound has been completely closed, the slider (3) is discarded and the rest of the device remains firmly fixed to the skin until the healing process has terminated, at which point it is finally removed.

What is claimed is:

1. An Incision and closure surgical device containing a slide fastener fitted to a self-adhesive flexible sheet, having a contact electrode for electrical coagulation supplied with a cutting surgical element, comprising a slider for said slide fastener which central partition wall or separator island includes a contact electrode having, a vertical segment that spans the full height of the main body of the said slider, and a horizontal segment which, extends rearward from the bottom end of the said vertical segment, is positioned beneath the contact surface area of the stringer tapes, and is fitted with a cutting edge, the said cutting edge being the active tip for applying electrical energy to the tissues and being located at the bottom and rear end of the slider, thereby always remaining underneath a closed segment of the slide fastener, whichever be the position of the slider along the stringer tapes.

2. A surgical device according to claim 1, wherein the said slide fastener comprises continuous cross section interlocking members along its stringer tapes.

3. A surgical device according to claim 1, wherein the front end of the said slide fastener comprises a rearward descending slope, at which site the flexible self-adhesive sheet grows thicker.

4. A surgical device according to claim 1, wherein the said vertical segment, that spans the full height of the main body of the slider, is the central core of the said separator island, without coming into contact with the stringer tapes.

5. A surgical device according to claim 1, wherein the upper end of the said vertical segment, protruding through the upper surface of the slider, comprises a terminal element for connection to an electrosurgical instrument.

6. A surgical device according to claim 1, wherein the whole surface area of the said electrode, with the exception of the cutting edge and the terminal element for connection to an electrosurgical instrument, is sheathed in an insulating material against electrical energy.

* * * * *